United States Patent
Ball et al.

(10) Patent No.: US 7,914,476 B2
(45) Date of Patent: Mar. 29, 2011

(54) PEDIATRIC DIGITAL WRAP

(76) Inventors: Darlene Ball, Coarsegold, CA (US); Yvonne Morris, Fresno, CA (US)

( * ) Notice: Subject to any disclaimer, the term of this patent is extended or adjusted under 35 U.S.C. 154(b) by 697 days.

(21) Appl. No.: 11/924,796

(22) Filed: Oct. 26, 2007

(65) Prior Publication Data

US 2008/0103424 A1 May 1, 2008

Related U.S. Application Data

(60) Provisional application No. 60/854,995, filed on Oct. 27, 2006.

(51) Int. Cl.
*A61F 5/37* (2006.01)
*A61F 5/00* (2006.01)
*A61F 13/06* (2006.01)
*A61B 19/00* (2006.01)
*A41D 13/08* (2006.01)
*A41D 19/00* (2006.01)
*A63B 23/14* (2006.01)
*A63B 23/16* (2006.01)

(52) U.S. Cl. .................. 602/61; 602/5; 602/20; 602/21; 602/22; 602/60; 602/62; 128/846; 128/869; 128/878; 128/879; 128/880; 482/44; 482/47; 2/16; 2/21; 2/163

(58) Field of Classification Search .................. 128/846, 128/869, 878–880; 602/5, 20–22, 60–62; 482/44, 47, 48, 148; 2/16, 21, 163; 473/54, 473/55, 59, 61
See application file for complete search history.

(56) References Cited

U.S. PATENT DOCUMENTS

| | | | | |
|---|---|---|---|---|
| 3,347,547 A * | 10/1967 | Hynes | ............................ | 482/47 |
| 4,549,537 A * | 10/1985 | Ender | ............................ | 602/21 |
| 4,867,150 A * | 9/1989 | Gilbert | ............................ | 602/47 |
| 5,697,103 A * | 12/1997 | Wiggins | ............................ | 2/159 |
| 6,248,932 B1 * | 6/2001 | Himmelsbach | ................ | 602/41 |
| 6,307,118 B1 * | 10/2001 | Reich | ............................ | 602/42 |
| 6,450,924 B1 * | 9/2002 | Block | ............................ | 482/48 |
| 6,913,582 B2 * | 7/2005 | Chen et al. | ........................ | 602/5 |
| 7,135,006 B1 * | 11/2006 | Weber et al. | ..................... | 602/22 |
| 7,431,657 B2 * | 10/2008 | Whitehead et al. | .............. | 473/59 |
| 7,537,577 B2 * | 5/2009 | Phelan et al. | .................... | 602/21 |
| 7,601,130 B2 * | 10/2009 | Farrell et al. | ..................... | 602/20 |
| 7,712,153 B2 * | 5/2010 | Adams, Jr. | ......................... | 2/163 |
| 7,731,633 B1 * | 6/2010 | Williams | ......................... | 482/47 |

* cited by examiner

*Primary Examiner* — Patricia M Bianco
*Assistant Examiner* — Brandon Jackson
(74) *Attorney, Agent, or Firm* — ShuffieldLowman; Matthew G. McKinney

(57) ABSTRACT

A pediatric digital wrap comprising a flexible T-shaped base member having a first end adapted to fold over and substantially cover a finger tip of a patient's injured digit. A removable insert comprising a layer of pressure sensitive adhesive with a non-adhesive center pad provides protection and padding for the injured digit. The removable insert is secured to the first side of the base member so that the insert is placed directly over the wound of the patient's digit when the first end is folded over the patient's finger tip. A finger strap wraps around the periphery of the patient's injured digit below the patient's finger tip and serves to secure the first end of the base member over the finger tip of the injured digit. A wrist strap is disposed perpendicular to the first end of the base member and adapted to wrap around a patient's wrist.

14 Claims, 3 Drawing Sheets

PEDIATRIC DIGITAL WRAP

CROSS-REFERENCED TO RELATED APPLICATIONS

This application claims the benefit of U.S. Provisional Application No. 60/854,995 filed Oct. 27, 2006. The disclosure of the provisional application is incorporated herein by reference.

BACKGROUND OF THE INVENTION

1. Field of the Invention

This invention relates generally to medical devices and more specifically to an apparatus that is used as a medical dressing wrap for an injured digit.

2. Description of the Prior Art

Fingertip amputation among children is a common injury. Many fingertip amputations can be classified consistent with the normal functional anatomy of the tip and perionychium. Injuries are classified according to where the amputation has occurred or whether the injury primarily involves the pulp (soft tissue) or nail bed. These classification systems refer to the zone and the plane of injury. For example, amputation injuries can be dorsal, transverse or volar, according to the plane of the amputation. The plane of the amputation and the condition of the tissue at the injury site help determine the best repair technique for these injuries.

The medical treatment for a finger tip amputation is typically cared for in part by applying an antibiotic ointment to the area and covering with gauze. The gauze is removed to soak the injury one or two times daily and to redress the wound. The dressing often times adheres to the wound making it painful to the patient to remove. Accordingly, it is very difficult for medical personnel to change the dressing on a child's finger while the pediatric patient is crying and moving in response to the pain. Therefore, what is needed in the art is an improved medical dressing that is comfortable, versatile and quick to apply.

There have been attempts to improve medical dressings such that improved efficiency and comfort is achieved. By way of example, note U.S. Pat. No. 5,807,296 to Stubbs, which discloses a method of stopping blood flow using a first aid mitt. Stubbs discloses a mitt with two opposing thumbs that is slipped over an injured left or right hand. An absorbent dressing is placed inside the mitt and proximate the end of the mitt to serve as a larger version of a cotton-tip swap. A shortcoming of this prior art is that the mitt must be slipped completely off to reapply the medical dressing and the mitt reduces the use of the patient's hand.

Another example is U.S. Pat. No. 5,921,948 to Kawaguchi, et al, which is directed to improving a surgical dressing using an adhesive tape. This is accomplished by using a polytetrafluoroethylene film having a specified low tensile strength that allows the adhesive tape to stretch accordingly. However, the adhesive tape of Kawaguchi is required to stick to the skin of the patient making it uncomfortable to remove and reapply on a daily basis.

Yet another example is U.S. Pat. No. 5,328,449 to Andrews et al., which discloses a wound dressing for the hands. Similar to Stubbs discussed above, Andrews discloses a mitt for covering a patient's hand. The entire mitt of Andrews is formed of three layers. A first layer is a porous polyethylene film, the second layer is an absorbent material and the third layer is a waterproof breathable material. A shortcoming of this prior art is that the entire medical dressing is removed and disposed of and not capable of reuse. Accordingly, what is needed in the art is a medical dressing that is reusable but remains sanitary.

Another shortcoming of the prior art is that the medical dressing can be removed by a child thereby inhibiting the healing process and exposing a wound to bacteria and infection. Accordingly, what is needed in the art is a medical dressing that is "child-proof."

Notwithstanding the existence of such prior art medical dressings, there is a need for an improved medical dressing that is easy to remove and reapply by medical personnel or care giver.

It is, therefore, to the effective resolution of the aforementioned problems and shortcomings of the prior art that the present invention is directed.

However, in view of the prior art at the time the present invention was made, it was not obvious to those of ordinary skill in the pertinent art bow the identified needs could be fulfilled.

SUMMARY OF THE INVENTION

This invention is a pediatric digital wrap comprised of a flexible T-shaped base member having a first end adapted to fold over and substantially cover a finger tip of a patient's injured digit. A pair of elastic strips disposed on a first side of the base member such that improved movement of the digit is achieved without reducing the efficacy of the dressing. A finger strap proximate to first end of T-shaped base member and disposed perpendicular to the first end so that the finger strap is adapted to wrap around the periphery of the patient's injured digit below the patient's finger tip and serves to secure first end of T-shaped base member over the finger tip of the injured digit. A finger strap fastening closure for securing the finger strap around the patient's injured digit comprises a finger loop at a first end of the finger strap and a finger latch at a second end of the finger strap interconnected by a first band.

The flexible T-shaped base member having a second end forming a wrist strap disposed perpendicular to the first end of the base member and adapted to wrap around a patient's wrist. The wrist strap further comprising a wrist strap closure for securing the wrist strap around the patient's wrist wherein the wrist strap closure comprising a wrist loop at a first end of wrist strap and a wrist latch at a second end of the wrist strap interconnected by a second band.

A palm strap interposed between the finger strap and the wrist strap and disposed perpendicular to the first end of the base member so that the palm strap is adapted to wrap around a patient's palm. The palm strap further comprising a palm strap closure for securing the palm strap around the patient's palm wherein the palm strap closure includes a palm loop at a first end of palm strap and a palm latch at a second end of palm strap interconnected by a third band. A removable insert having a comparable width of the first end and comprising a layer of pressure sensitive adhesive with an atraumatic non-adhesive center pad dressing that provides protection and padding for the injured digit is secured to the first side of the base member so that insert is placed directly over the wound of the patient's digit when the first end is folded over the patient's finger tip.

It is therefore an object of the present invention to provide for an improvement that overcomes the aforementioned inadequacies of the prior art and provides a significant contribution to the advancement of pediatric medical dressings.

Another object of the present invention is to provide a surgical dressing that is reusable but remains sanitary.

Another object of the present invention is to provide a medical dressing that is "child-proof."

Another object of the present invention is to provide a medical dressing that is easy to remove and reapply by medical personnel or care giver.

Both the foregoing general description and the following detailed description are explanatory and are not restrictive of the invention as claimed. The accompanying drawings, which are incorporated in and constitute part of the specification, illustrate embodiments of the present invention and together with the general description, serve to explain principles of the present invention.

These and other important objects, advantages, and features of the invention will become clear as this description proceeds.

The invention accordingly comprises the features of construction, combination of elements, and arrangement of parts that will be exemplified in the description set forth hereinafter and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which.

DETAILED DESCRIPTION OF THE PREFERRED EMBODIMENT

Figure 1:
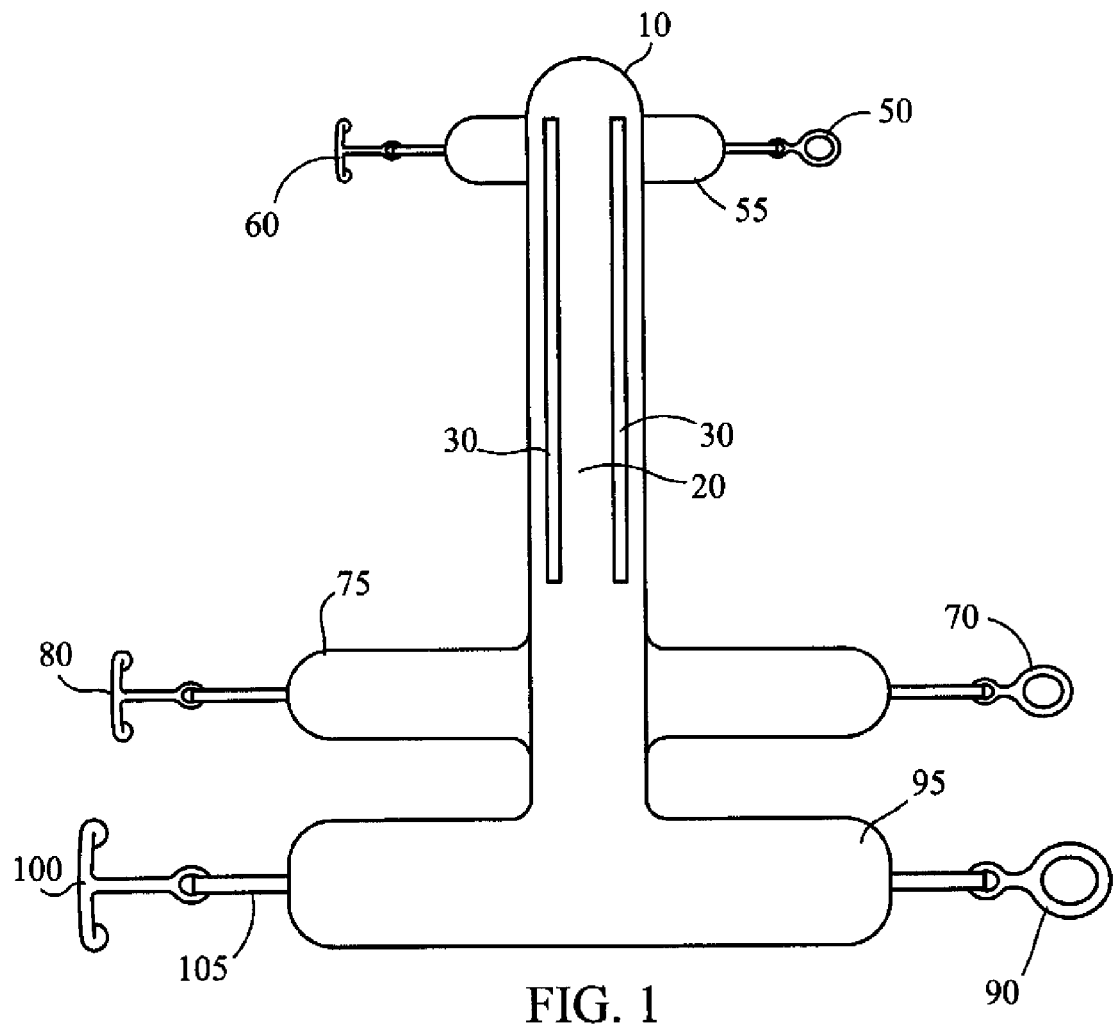
FIG. 1 is a plan view of a first side of the pediatric digital wrap of an embodiment of the present invention.

FIG. 1 shows a first side of the pediatric digital wrap of the present invention, which is placed adjacent to the patient's skin. The pediatric digital wrap is comprised of a flexible T-shaped base member 20 having a first end 10 adapted to fold over and substantially cover the tip of a patient's injured digit. T-shaped base member 20 further comprises a pair of elastic strips 30 that are disposed thereon such that for improved movement of the digit without reducing the efficacy of the dressing. In the preferred embodiment, base member 20 comprises a non-porous material to prevent the patient's wound exudate from leaching through the medical dressing.

Finger strap 55 is proximate to first end 10 of T-shaped base member 20 and is disposed perpendicular to first end 10. Finger strap 55 is adapted to wrap around the periphery of the patient's injured digit below the patient's finger tip and serves to secure first end 10 of T-shaped base member 20 over the tip of the injured digit. Finger strap 55 further comprises a finger strap fastening closure for securing finger strap 55 around the patient's injured digit. In the preferred embodiment, the finger strap closure comprises a finger loop 50 at a first end of finger strap 55 and a finger latch 60 at a second end of finger strap 55. Finger latch 60 is twisted to slip through finger loop 50 so that once finger latch 60 passes completely though finger loop 50, flanges of finger latch 60 are positioned such that finger latch 60 cannot unintentionally slip back through finger loop 50. In alternative embodiments, finger strap closures include hook and loop material, buttons, snaps, and/or fabric, among other examples.

Second end 95 of the T-shaped base member 20 is disposed perpendicular to first end 10 of the base member 20 and is adapted to wrap around the patient's wrist and proximal segment of the hand consisting of the carpal bones and the associated soft parts. Wrist strap 95 further comprises a wrist strap closure for securing wrist strap 95 around the patient's wrist. In the preferred embodiment, the wrist strap closure comprises a wrist loop 90 at a first end of wrist strap 95 and a wrist latch 100 at a second end of wrist strap 95. Wrist latch 100 is twisted to slip through wrist loop 90 so that once wrist latch 100 passes completely though wrist loop 90, flanges of wrist latch 100 are positioned such that wrist latch 100 cannot unintentionally slip back through wrist loop 90. In alternative embodiments, wrist strap closures include hook and loop material, buttons, snaps, and/or fabric, among other examples.

Palm strap 75 is interposed between finger strap 55 and second end 95 and similarly disposed perpendicular to first end 10 of base member 20 and is adapted to wrap around a patient's palm and flexor surface of the hand. Similar to finger strap 55, palm strap 75 further comprises a palm strap closure for securing palm strap 75 around the patient's palm. In the preferred embodiment, the palm strap closure comprises a palm loop 70 at a first end of palm strap 75 and a palm latch 80 at a second end of palm strap 75. Palm latch 80 is twisted to slip through palm loop 70 so that once palm latch 80 passes completely though palm loop 70, flanges of palm latch 80 are positioned such that palm latch 80 cannot unintentionally slip back through palm loop 70. In alternative embodiments, palm strap closures include hook and loop material, buttons, snaps, and/or fabric, among other examples.

Figure 2:
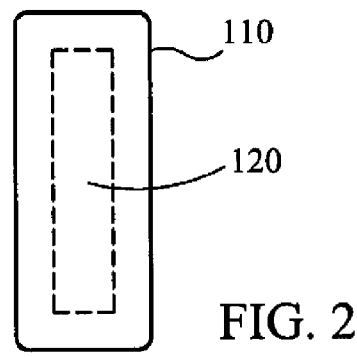
FIG. 2 is a plan view of an insert for the pediatric digital wrap of an embodiment of the present invention.

Referring now to FIG. 2, a removable insert 110 having a comparable width of first end 10 comprises a layer of pressure sensitive adhesive with a non-adhesive center pad 120 that provides protection and padding for the injured digit while maximizing absorbency, wicking and dispersal of wound exudate. Removable insert 110 is secured to a first side of T-shaped base member 20 so that insert 110 is placed directly over the wound of a patient's digit when first end 10 is folded over the patient's finger tip. Insert 110 is secured to base member 20 using the layer of pressure sensitive adhesive.

In use, insert 110 can be easily removed and a new insert reapplied by uncoupling finger strap fastening closure 50, 60 so that finger strap 55 is loose and first end 10 is pulled back from the patient's finger tip. Palm strap 75 and wrist strap 95 remain securely in place when insert 110 is being changed. Once first end 10 is removed from the finger tip, first side of T-shaped base member 20 is exposed so that insert 110 can be peeled from base member 20 and a new insert 110 reapplied.

Figure 3:
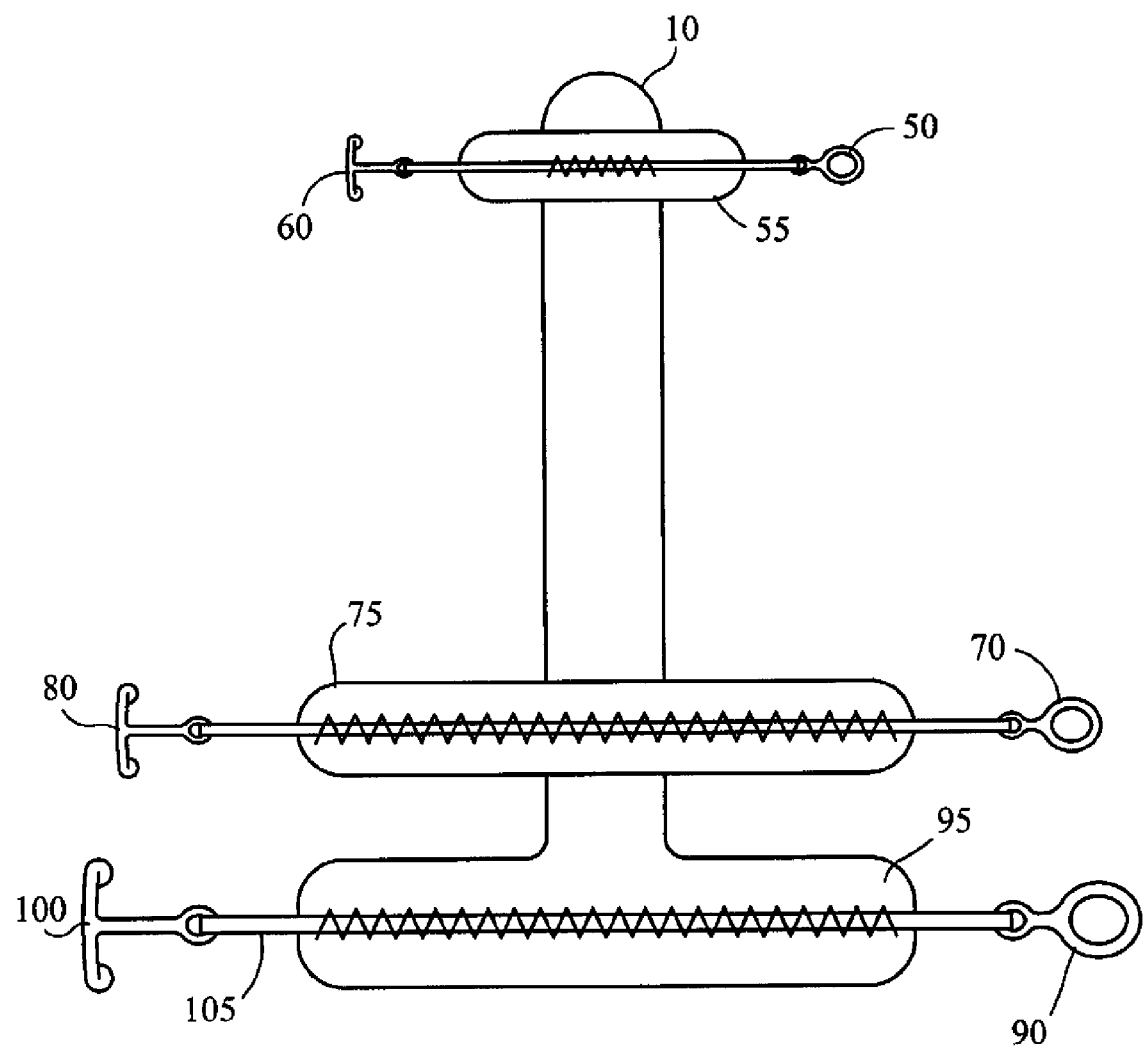
FIG. 3 is a plan view of a second side of the pediatric digital wrap of an embodiment of the present invention.

FIG. 3 shows a second side of the medical dressing of the present invention, which faces away from the patient's skin when the medical dressing is secured into place. The medical dressing is comprised of a first end 10 adapted to fold over and substantially cover the tip of a patient's injured digit. Finger strap 55 is proximate to first end 10 and is disposed perpendicular to first end 10. Finger strap 55 is adapted to wrap around the periphery of the patient's injured digit below the patient's finger tip and serves to secure first end 10 over the tip of the injured digit. Finger strap 55 further comprises a finger strap fastening closure for securing finger strap 55 around the patient's injured digit. The finger strap closure comprises a finger loop 50 at a first end of finger strap 55 and a finger latch 60 at a second end of finger strap 55, which are interconnected by a band. Stitching is used to secure finger strap 55 and finger strap closure to first end 10. However, adhesive is another suitable means to attach finger strap 55 and/or finger strap closure to first end 10. Finger latch 60 is twisted to slip through finger loop 50 so that once finger latch 60 passes completely though finger loop 50, flanges of finger latch 60 are positioned such that finger latch 60 cannot unintentionally slip back through finger loop 50.

A wrist strap 95 of the medical dressing is disposed perpendicular to first end 10 and is adapted to wrap around the patient's wrist. Wrist strap 95 further comprises a wrist strap closure for securing wrist strap 95 around the patient's wrist. The wrist strap closure comprises a wrist loop 90 at a first end of wrist strap 95 and a wrist latch 100 at a second end of wrist strap 95, which are interconnected by a band. Stitching is used to secure wrist strap closure to wrist strap 95. However, adhesive is another suitable means to attach wrist strap closure to wrist strap 95. Wrist latch 100 is twisted to slip through wrist loop 90 so that once wrist latch 100 passes completely though wrist loop 90, flanges of wrist latch 100 are positioned such that wrist latch 100 cannot unintentionally slip back through wrist loop 90.

Palm strap 75 is interposed between finger strap 55 and second end 95 and similarly disposed perpendicular to first end 10 and is adapted to wrap around a patient's palm and flexor surface of the hand. Similar to finger strap 55, palm strap 75 further comprises a palm strap closure for securing palm strap 75 around the patient's palm. The palm strap closure comprises a palm loop 70 at a first end of palm strap 75 and a palm latch 80 at a second end of palm strap 75, which are connected by a band. Stitching is used to secure palm strap 75 and palm strap closure to first end 10. However, adhesive is another suitable means to attach palm strap 75 and/or palm strap closure to first end 10. Palm latch 80 is twisted to slip through palm loop 70 so that once palm latch 80 passes completely though palm loop 70, flanges of palm latch 80 are positioned such that palm latch 80 cannot unintentionally slip back through palm loop 70.

Figure 4:
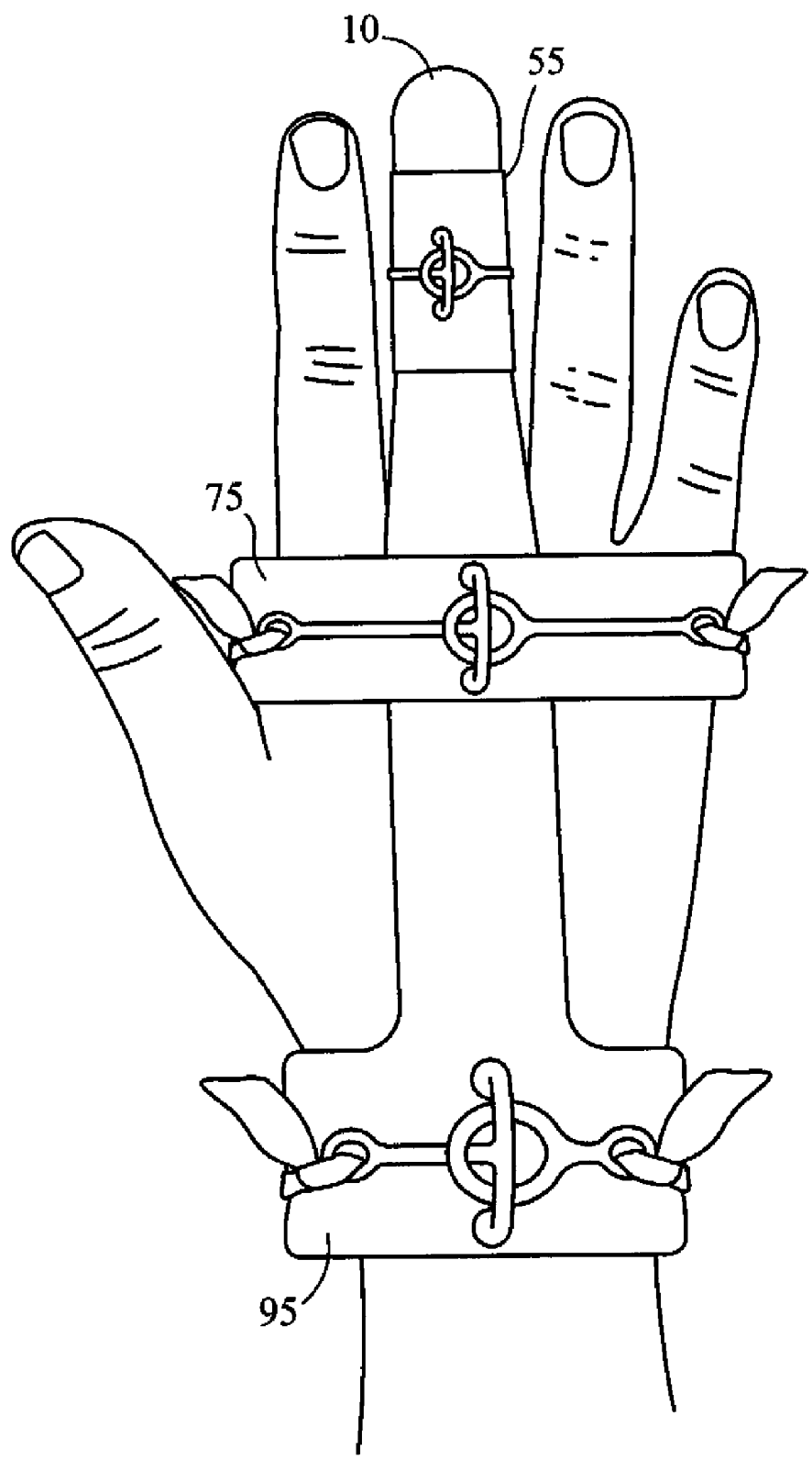
FIG. 4 is a perspective view of the pediatric digital wrap showing applied to a patient's hand.

Referring now to FIG. 4, the medical dressing is secured to a patient's hand. First end 10 is folded over the finger tip of the patient and finger strap 55 overlays first end 10 securing it in place. Finger strap closure is coupled together firmly on the outside of the patient's hand and adapted to provide resistance to a child removing finger strap 55. Palm strap 75 is wrapped around the patient's hand and positioned so that the medical dressing remains in place but allows for a full range of motion for the patient's hand. Wrist strap 95 is shown around the patient's wrist and wrist strap closure prevents a pediatric patient from easily removing the dressing.

The particular embodiments disclosed above and in the drawings are illustrative only, as the invention may be modified and practiced in different but equivalent manners apparent to those skilled in the art having the benefit of the teachings herein. Furthermore, no limitations are intended to the details of construction or design herein shown. It is therefore evident that the particular embodiments disclosed above may be altered or modified and all such variations are considered within the scope and spirit of the invention.

It is also to be understood that the following claims are intended to cover all of the generic and specific features of the invention herein described, and all statements of the scope of the invention, which as a matter of language, might be said to fall there between.

Now that the invention has been described,
What is claimed is:

1. A pediatric digital wrap comprising:
   a flexible T-shaped base member having a first end adapted to fold over and substantially cover a finger tip of a patient's injured digit;
   a finger strap proximate to the first end of the base member and disposed perpendicular to the first end of the base member, wherein the finger strap is adapted to wrap around a periphery of the injured digit below the patient's finger tip and serves to secure the first end of the base member over the finger tip of the injured digit;
   the base member having a second end forming a wrist strap disposed perpendicular to the first end of the base member and adapted to wrap around a patient's wrist;
   a palm strap interposed between the finger strap and the wrist strap and disposed perpendicular to the first end of the base member, wherein the palm strap is adapted to wrap around a patient's palm;
   a removable insert having a comparable width of the first end of the base member and comprising a layer of pressure sensitive adhesive with a non-adhesive center pad that provides protection and padding for the injured digit, wherein the removable insert is secured to a first side of the base member so that the insert is placed directly over a wound of the patient's injured digit when the first end of the base member is folded over the patient's finger tip; and
   a pair of elastic strips disposed on a first side of the base member such that improved movement of the digit is achieved without reducing the efficacy of a dressing.

2. The pediatric digital wrap of claim 1, further comprising a finger strap closure for securing the finger strap around the patient's injured digit wherein the finger strap closure having a finger loop at a first end of the finger strap and a finger latch at a second end of the finger strap interconnected by a first band.

3. The pediatric digital wrap of claim 2, further comprising a wrist strap closure for securing the wrist strap around the patient's wrist wherein the wrist strap closure comprising a wrist loop at a first end of the wrist strap and a wrist latch at a second end of the wrist strap interconnected by a second band.

4. The pediatric digital wrap of claim 3, further comprising a palm strap closure for securing the palm strap around the patient's palm wherein the palm strap closure comprising a palm loop at a first end of the palm strap and a palm latch at a second end of the palm strap interconnected by a third band.

5. The pediatric digital wrap of claim 1 further comprising a finger strap closure for securing the finger strap around the patient's injured digit comprising hook and loop fasteners enabling adjustable closing and opening of the finger strap for various sized fingers and comfortable fit.

6. The pediatric digital wrap of claim 5 further comprising a wrist strap closure for securing the wrist strap around the patient's wrist wherein the wrist strap closure comprising hook and loop fasteners enabling adjustable closing and opening of the wrist strap for various sized wrists and comfortable fit.

7. The pediatric digital wrap of claim 6 further comprising a palm strap closure for securing the palm strap around the patient's palm wherein the palm strap closure comprising hook and loop fasteners enabling adjustable closing and opening of the wrist strap for various sized palms and comfortable fit.

8. The pediatric digital wrap of claim 1, wherein the base member is comprised of an elastic material.

9. The pediatric digital wrap of claim 1, wherein the center pad of the insert is comprised of non-woven material.

10. A method of applying a pediatric digital wrap, the method comprising:
   providing a flexible T-shaped base member having a first end adapted to fold over and substantially cover a finger tip of a patient's injured digit;

providing a finger strap proximate to the first end of the base member and disposed perpendicular to the first end of the base member, wherein the finger strap is adapted to wrap around a periphery of the injured digit below the patient's finger tip and serves to secure the first end of the base member over the finger tip of the injured digit;

providing a wrist strap disposed perpendicular to the first end of the base member and adapted to wrap around a patient's wrist;

providing a palm strap interposed between the finger strap and the wrist strap and disposed perpendicular to the first end of the base member, wherein the palm strap is adapted to wrap around a patient's palm;

providing a removable insert having a comparable width of the first end of the base member and comprising a layer of pressure sensitive adhesive with a non-adhesive center pad that provides protection and padding for the injured digit, wherein the removable insert is secured to a first side of the base member so that the insert is placed directly over a wound of the patient's injured digit when the first end of the base member is folded over the patient's finger tip; and providing a pair of elastic strips disposed on a first side of the base member such that improved movement of the digit is achieved without reducing the efficacy of a dressing.

11. The method of claim 10 further comprising providing a finger strap closure for securing the finger strap around the patient's injured digit wherein the finger strap closure having a finger loop at a first end of the finger strap and a finger latch at a second end of the finger strap interconnected by a first band.

12. The method of claim 11 further comprising providing a wrist strap closure for securing the wrist strap around the patient's wrist wherein the wrist strap closure comprising a wrist loop at a first end of the wrist strap and a wrist latch at a second end of the wrist strap interconnected by a second band.

13. The method of claim 12 further comprising providing a palm strap closure for securing the palm strap around the patient's palm wherein the palm strap closure comprising a palm loop at a first end of the palm strap and a palm latch at a second end of the palm strap interconnected by a third band.

14. A pediatric digital wrap comprising:

a flexible T-shaped base member having a first end adapted to fold over and substantially cover a finger tip of a patient's injured digit;

a pair of elastic strips disposed on a first side of the base member such that improved movement of the digit is achieved without reducing the efficacy of a dressing;

a finger strap proximate to the first end of the base member and disposed perpendicular to the first end of the base member wherein the finger strap is adapted to wrap around a periphery of the patient's injured digit below the finger tip and serves to secure the first end of the base member over the finger tip of the injured digit;

a finger strap closure for securing the finger strap around the patient's injured digit wherein the finger strap closure having a finger loop at a first end of the finger strap and a finger latch at a second end of the finger strap interconnected by a first band;

the base member having a second end forming a wrist strap disposed perpendicular to the first end of the base member and adapted to wrap around a patient's wrist;

a wrist strap closure for securing the wrist strap around the patient's wrist, wherein the wrist strap closure comprising a wrist loop at a first end of the wrist strap and a wrist latch at a second end of the wrist strap interconnected by a second band;

a palm strap interposed between the finger strap and the wrist strap and disposed perpendicular to the first end of the base member, wherein the palm strap is adapted to wrap around a patient's palm;

a palm strap closure for securing the palm strap around the patient's palm wherein the palm strap closure comprising a palm loop at a first end of palm strap and a palm latch at a second end of palm strap interconnected by a third band; and a removable insert having a comparable width of the first end of the base member and comprising a layer of pressure sensitive adhesive with a non-adhesive center pad that provides protection and padding for the injured digit, wherein the removable insert is secured to the first side of the base member so that the insert is placed directly over a wound of the patient's injured digit when the first end of the base member is folded over the patient's finger tip.

* * * * *